(12) United States Patent
Bradfield et al.

(10) Patent No.: US 10,125,395 B2
(45) Date of Patent: Nov. 13, 2018

(54) GENETIC ALTERATIONS AND METHODS OF USE THEREOF FOR THE DIAGNOSIS AND TREATMENT OF TYPE I DIABETES

(71) Applicant: The Children's Hospital of Philadelphia, Philadelphia, PA (US)

(72) Inventors: Jonathan Bradfield, Philadelphia, PA (US); Struan Grant, Philadelphia, PA (US); Hakon Hakonarson, Malvern, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/352,707

(22) PCT Filed: Oct. 18, 2012

(86) PCT No.: PCT/US2012/060825
§ 371 (c)(1),
(2) Date: Apr. 18, 2014

(87) PCT Pub. No.: WO2013/059469
PCT Pub. Date: Apr. 25, 2013

(65) Prior Publication Data
US 2014/0255387 A1   Sep. 11, 2014

Related U.S. Application Data

(60) Provisional application No. 61/548,457, filed on Oct. 18, 2011.

(51) Int. Cl.
| | | |
|---|---|---|
| C07H 21/02 | (2006.01) | |
| C07H 21/04 | (2006.01) | |
| *C12Q 1/6883* | (2018.01) | |
| C12P 19/34 | (2006.01) | |
| C12Q 1/68 | (2018.01) | |

(52) U.S. Cl.
CPC ..... *C12Q 1/6883* (2013.01); *C12Q 2600/156* (2013.01)

(58) Field of Classification Search
CPC .................. C12Q 1/6883; C12Q 2600/156
See application file for complete search history.

(56) References Cited

U.S. PATENT DOCUMENTS

2001/0053519 A1* 12/2001 Fodor .................. B01J 19/0046
435/6.11

OTHER PUBLICATIONS

Submitted SNP(ss) Details: ss244290195 (Jun. 10, 2010) from dbSNP, www.ncbi.nlm.nih.gov. pp. 1-2.*
Armstrong, B. et al. Cytometry 40:102-108 (2000).*
Velez D.R. et al. American Journal of Obstetrics and Gynecology, vol. 200, Issue 2, Feb. 2009, pp. 209.e1-209.e27.*
Submitted SNP(ss) Report in Submission Format, NCBI Assay Id(ss#): ss244290195, Jun. 10, 2010.*
Barrett et al., Genome-wide association study and meta-analysis find that over 40 loci affect risk of type 1 diabetes, Nat Genet, 2009, 703-7, 41(6).
Grant et al., Follow-up analysis of genome-wide association data identifies novel loci for type 1 diabetes, Diabetes, 2009, 290-5, 58(1).
Hakonarson et al., A novel susceptibility locus for type 1 diabetes on Chr12q13 identified by a genome-wide association study, Diabetes, 2008, 1143-6, 57(4).
Hakonarson et al., A genome-wide association study identifies KIAA0350 as a type 1 diabetes gene, Nature, 2007 591-4, 448(7153).

* cited by examiner

*Primary Examiner* — Stephen T Kapushoc
(74) *Attorney, Agent, or Firm* — Kathleen D. Rigaut; Dann, Dorfman, Herrell & Skillman (57) ABSTRACT

Compositions and methods for the diagnosis and treatment of T1D are disclosed. More specifically, the invention provides gene targets containing single nucleotide polymorphisms associated with this disease. Methods and kits for using the sequences so identified for diagnostic and therapeutic purposes are also provided.

4 Claims, 3 Drawing Sheets

GENETIC ALTERATIONS AND METHODS OF USE THEREOF FOR THE DIAGNOSIS AND TREATMENT OF TYPE I DIABETES

This application is a § 371 national phase entry of PCT/US2012/60825 filed Oct. 18, 2012, which claims priority to U.S. Provisional Application No. 61/548,457 filed Oct. 11, 2011, each of which is incorporated by reference herein.

FIELD OF THE INVENTION

This invention relates to the fields of glucose metabolism, genetics and pathology associated with diabetes, particularly type I diabetes. More specifically, the invention provides gene targets containing single nucleotide polymorphisms which had heretofore not been associated with this disease. Methods and kits for using the sequences so identified for diagnostic and therapeutic purposes are also provided.

BACKGROUND OF THE INVENTION

Several publications and patent documents are cited throughout the specification in order to describe the state of the art to which this invention pertains. Each of these citations is incorporated herein by reference as though set forth in full.

Type I diabetes (T1D) results from the autoimmune destruction of pancreatic beta cells, a process believed to be strongly influenced by multiple genes and environmental factors. The incidence of T1D has been increasing in Western countries and has more than doubled in the United States over the past 30 years. The disease shows a strong familial component, with first-degree relatives of cases being at 15 times greater risk of T1D than a randomly selected member of the general population and monozygotic twins being concordant for T1D at a frequency of approximately 50%. However, while the genetic evidence is strong, the latter data suggests that an interplay with environmental factors also plays a key role in influencing T1D outcome.

The familial clustering of T1D is influenced by multiple genes. Variation in four loci has already been established to account for a significant proportion of the familial aggregation of T1D. These include the major histocompatibility complex (MHC) region on 6p21 (including the HLA-DRB1, -DQA1 and -DRQ1 genes); the insulin/insulin-like growth factor 2 gene complex (INS-IGF2) on 11p15, the protein tyrosine phosphatase-22 (PTPN22) gene on 1p13 and the gene encoding cytotoxic T-lymphocyte-associated protein 4 (CTLA4) on 2q31. The interleukin-2 receptor alpha (CD25) locus on 10p15 has also been implicated in the pathogenesis of T1D but remains to be replicated by independent studies. In addition, spontaneous mouse model studies of T1D have implicated numerous other regions that have been confirmed in replication studies. Several other loci have also been implicated in human association studies with T1D but the effects of these implicated genes remain controversial and are subject to confirmation in independent studies utilizing sufficient sample sizes. Together, these studies suggest that many more T1D susceptibility genes remain to be discovered.

SUMMARY OF THE INVENTION

In accordance with the present invention, T1D-associated SNPs have been identified which are indicative of an altered risk of developing T1D. Thus, in one aspect, nucleic acids comprising at least one genetic alteration identified in Table 1 are provided. Such nucleic acids and the proteins encoded thereby have utility in the diagnosis and management of type 1 diabetes (T1D).

In another aspect of the invention, methods for assessing susceptibility for developing T1D are provided. An exemplary method entails providing a target nucleic acid from a patient sample, said target nucleic acid having a predetermined sequence in the normal population, and assessing said target nucleic acid for the presence of at least one genetic alteration, e.g., a single nucleotide polymorphism, which is indicative of an altered risk of developing T1D. Such genetic alterations can also include, without limitation, inversion, deletion, duplication, and insertion of at least one nucleotide in said sequence.

Preferably, the genetic alteration is a single nucleotide polymorphism present in LMO7 or EFR3B encoding nucleic acids and genetic regions associated therewith. In another embodiment the SNP is in region 6q27 in linkage with the IDDM8 region. Preferably, the SNPs are selected from those shown in Table 1.

The methods of the invention also include the detection of any of the T1D associated genetic alterations comprising the single nucleotide polymorphisms set forth in Table 1 for the diagnosis of T1D. Kits and microarrays for practicing the foregoing methods are also provided.

In yet another embodiment, a method of managing T1D is provided which entails administering a therapeutic agent to a patient in need thereof. The therapeutic agent can be a small molecule, an antibody, a protein, an oligonucleotide, or a siRNA molecule.

In another aspect of the invention, a method for identifying agents that bind and/or modulate LMO7 or EFR3B functional activity is provided, as well as pharmaceutical compositions comprising said agent in a biologically acceptable carrier.

DETAILED DESCRIPTION OF THE INVENTION

In efforts to identify additional genetic loci associated with T1D, a large combined T1D cohort was assessed for replication of all previously unknown T1D loci with p values $<1.0\times10^{-05}$. These studies revealed new genetic variants associated with T1D which are listed in Table 1. Also disclosed are methods of use of nucleic acid molecules and proteins encoded thereby in diagnostic and screening assays.

Definitions

The following definitions are provided to facilitate an understanding of the present invention:

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"T1D-associated SNP or specific marker" is a SNP or marker which is associated with an increased or decreased risk of developing TED not found normal patients who do not have this disease. Such markers may include but are not limited to nucleic acids, proteins encoded thereby, or other small molecules.

The phrase "Type 1 diabetes (T1D)" refers to a chronic (lifelong) disease that occurs when the pancreas produces too little insulin to regulate blood sugar levels appropriately. T1D, often called juvenile or insulin-dependent diabetes results from altered metabolism of carbohydrates (including sugars such as glucose), proteins, and fats. In type 1 diabetes, the beta cells of the pancreas produce little or no insulin, the hormone that allows glucose to enter body cells. Once glucose enters a cell, it is used as fuel. Without adequate insulin, glucose builds up in the bloodstream instead of going into the cells. The body is unable to use this glucose for energy despite high levels in the bloodstream, leading to increased hunger. In addition, high levels of glucose in blood causes the patient to urinate more, which in turn causes excessive thirst. Within 5 to 10 years after diagnosis, the insulin-producing beta cells of the pancreas are completely destroyed, and no more insulin is produced.

Type 1 diabetes can occur at any age, but it usually starts in people younger than 30. Symptoms are usually severe and occur rapidly. The exact cause of type 1 diabetes is not known. Type 1 diabetes accounts for 3% of all new cases of diabetes each year. There is 1 new case per every 7,000 children per year. New cases are less common among adults older than 20.

A "single nucleotide polymorphism (SNP)" refers to a change in which a single base in the DNA differs from the usual base at that position. These single base changes are called SNPs or "snips." Millions of SNP's have been cataloged in the human genome. Some SNPs such that which causes sickle cell are responsible for disease. Other SNPs are normal variations in the genome.

The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with T1D. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form. By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any T1D specific marker gene or nucleic acid, but does not hybridize to other bovine nucleotides. Also polynucleotide which "specifically hybridizes" may hybridize only to a T1D specific marker, such a T1D-specific marker shown in Table 1. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$T_m$=81.5° C.+16.6 Log [Na+]+0.41(% G+C)−0.63(% formamide)−600/#bp in duplex

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the T1D specific marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the T1D specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. "Sample" or "patient sample" or "biological sample" generally refers to a sample which may be tested for a particular molecule, preferably a T1D specific marker molecule, such as a marker shown in Table 1. Samples may include but are not limited to cells, body fluids, including blood, serum, plasma, urine, saliva, tears, pleural fluid and the like.

Methods of Using T1D-Associated SNPS for T1D Detection Assays

T1D SNP containing nucleic acids, including but not limited to those listed in Table 1, may be used for a variety of purposes in accordance with the present invention. T1D-associated SNP containing DNA, RNA, or fragments thereof may be used as probes to detect the presence of and/or expression of T1D specific markers. Methods in which T1D specific marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting T1D-associated SNPs may be conducted on any type of biological sample, including but not limited to body fluids (including blood, urine, serum, gastric lavage), any type of cell (such as white blood cells, mononuclear cells) or body tissue.

From the foregoing discussion, it can be seen that T1D associated SNP containing nucleic acids, vectors expressing the same, T1D SNP containing marker proteins and anti-T1D specific marker antibodies of the invention can be used to detect T1D associated SNPs in body tissue, cells, or fluid, and alter T1D SNP containing marker protein expression for purposes of assessing the genetic and protein interactions involved in T1D.

In most embodiments for screening for T1D-associated SNPs, the T1D-associated SNP containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art. Alternatively, new detection technologies can overcome this limitation and enable analysis of small samples containing as little as 1 µg of total RNA. Using Resonance Light Scattering (RLS) technology, as opposed to traditional fluorescence techniques, multiple reads can detect low quantities of mRNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify T1D-associated SNP marker expression and accordingly, detect T1D.

Methods of Using T1D-Associated SNPS for Development of Therapeutic Agents

Since the SNPs identified herein have been associated with the etiology of T1D, methods for identifying agents that modulate the activity of the genes and their encoded products containing such SNPs should result in the generation of efficacious therapeutic agents for the treatment of a variety of disorders associated with this condition.

The chromosomal regions identified herein provide suitable targets for the rational design of therapeutic agents. For example, small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNP containing nucleic acids based on conformation or key amino acid residues required for function. A combinatorial chemistry approach will be used to identify molecules with greatest activity and then iterations of these molecules will be developed for further cycles of screening.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered T1D associated gene. These host cell lines or cells are defective at the polypeptide level. The host cell lines or cells are grown in the presence of drug compound. The rate of cellular metabolism of the host cells is measured to determine if the compound is capable of regulating cellular metabolism (or another cellular parameter associated with diabetes) in the defective cells. Host cells contemplated for use in the present invention include but are not limited to bacterial cells, fungal cells, insect cells, mammalian cells, pancreatic cells, and plant cells. The T1D-associated SNP encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of the SNP encoding nucleic acids on glucose metabolism and methods of use thereof for drug discovery are provided. Such cells and cell lines will be transfected with the SNP encoding nucleic acids described herein and the effects on glucagon secretion, insulin secretion and/or beta cell apoptosis can be determined. Such cells and cell lines will also be contacted with the siRNA molecules provided herein to assess the effects thereof on glucagon secretion, insulin secretion and/or beta cell apoptosis. The siRNA molecules will be tested alone and in combination of 2, 3, 4, and 5 siRNAs to identify the most efficacious combination for down regulating the target genes disclosed herein. Cells suitable for these purposes include, without limitation, INS cells (ATCC CRL 11605), PC12 cells (ATCC CRL 1721), MIN6 cells, alpha-TC6 cells and INS-1 832/13 cells (Fernandez et al., J. of Proteome Res. (2007). 7:400-411). Pancreatic islet cells can be isolated and cultured as described in Joseph, J. et al., (J. Biol. Chem. (2004) 279: 51049). Diao et al. (J. Biol. Chem. (2005) 280:33487-33496), provide methodology for assessing the effects of the SNP encoding nucleic acids and/or the siRNAs provided herein on glucagon secretion and insulin secretion. Park, J. et al. (J. of Bioch. and Mol. Biol. (2007) 40:1058-68) provide methodology for assessing the effect of these nucleic acid molecules on glucosamine induced beta cell apoptosis in pancreatic islet cells.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and Saccharomyces promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the T1D-associated SNPs of the present invention or functional fragments thereof provide a system in which to screen potential compounds or agents for the ability to modulate the development of T1D. Thus, in one embodiment, the nucleic acid molecules of the invention may be used to create recombinant cell lines for use in assays to identify agents which modulate aspects of EFR3B (UniProt identification no. Q9Y2G0) and LMO7 (GenBank Accession No. NM_005358) function. Notably, siRNA and shRNA molecules against LMO7 and EFR3B are commercially available from Santa Cruz Biotechnology. Such molecules are useful for the screening assays of the invention. Also provided herein are methods to screen for compounds capable of modulating the function of proteins encoded by the SNP containing nucleic acids described below.

Another approach entails the use of phage display libraries engineered to express fragment of the polypeptides encoded by the SNP containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of SNP containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of T1D-associated SNP containing nucleic acids enables the production of strains of laboratory mice carrying the T1D-associated SNPs of the invention. Transgenic mice expressing the T1D-associated SNP of the invention provide a model system in which to examine the role of the protein encoded by the SNP containing nucleic acid in the development and progression towards T1D. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes, including: aberrant lipid deposition, altered cellular metabolism and glucose regulation. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of T1D-associated SNP containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated T1D-associated SNP genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing T1D-associated SNP containing nucleic acid as a targeted insertional cassette provides means to detect a successful insertion as visualized, for example, by acquisition of immunoreactivity to an antibody immunologically specific for the polypeptide encoded by T1D-associated SNP nucleic acid and, therefore, facilitates screening/selection of ES cells with the desired genotype.

As used herein, a knock-in animal is one in which the endogenous murine gene, for example, has been replaced with human T1D-associated SNP containing gene of the invention. Such knock-in animals provide an ideal model system for studying the development of T1D.

As used herein, the expression of a T1D-associated SNP containing nucleic acid, fragment thereof, or a T1D-associated SNP fusion protein can be targeted in a "tissue specific manner" or "cell type specific manner" using a vector in which nucleic acid sequences encoding all or a portion of T1D-associated SNP are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

The nucleic acid sequence encoding the T1D-associated SNP of the invention may be operably linked to a variety of different promoter sequences for expression in transgenic animals. Such promoters include without limitation, a platelet-derived growth factor B gene promoter, described in U.S. Pat. No. 5,811,633; a brain specific dystrophin promoter, described in U.S. Pat. No. 5,849,999; a Thy-1 promoter; a PGK promoter; and a CMV promoter.

Methods of use for the transgenic mice of the invention are also provided herein. Transgenic mice into which a nucleic acid containing the T1D-associated SNP or its encoded protein have been introduced are useful, for example, to develop screening methods to screen therapeutic agents to identify those capable of modulating the development of T1D.

Kits and Articles of Manufacture

Any of the aforementioned products can be incorporated into a kit which may contain an T1D-associated SNP specific marker polynucleotide or one or more such markers immobilized on a solid support or Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

The following examples are provided to illustrate certain embodiments of the invention. They are not intended to limit the invention in any way.

Example I

Type 1 diabetes is an autoimmune disease leading to the destruction of the pancreatic islets. The prevalence of T1D in the United States in individuals below the age 20 is 1.7 per 1000. Genome wide association studies (GWAs) have been particularly valuable in identifying the genetic susceptibility loci underlying type 1 diabetes with over 40 associations described in the last two years. One inherent limitation to GWAs is the large sample sizes required to detect loci of modest effect. Meta-analyses are the most efficient and economical way to assemble such large cohorts. In an effort to find more loci, we analyzed the largest combined T1D cohort to date, totaling 10,000 cases and 17,500 controls, comprising ~14000 samples (~3500 cases, ~10500 controls) genotyped on Affymetrix 500K chips (GoKinD, WTCCC) and ~13500 samples (~6500 cases, ~7000 controls) genotyped on Illumina 550K chips (McGill/CHOP, DCCT-EDIC, TIDGC). A cohort of ~1000 independent trios (T1DGC/McGill) was used for replication of all previously unknown T1D loci with $p<1.0\times10^{-05}$. Power calculations based on these sample sizes indicate we have greater than 80% power to detect a variant with relative risk of 1.13 and above assuming a minor allele frequency of 20%. Methodologically, we initially inputted all datasets up to the 2 million CEU Hapmap SNPs using Mach 1.0 so that platform independent comparisons could be made. To control for population stratification, we used principal components analysis (PCA) in the Illumina and Affymetrix cohorts separately. The results of the PCA analysis were then used as covariates in a logistic regression. Summary stats were then computed on the Illumina and Affymetrix cohorts and combined at all 2 million SNPs using fixed-effects meta-analysis.

Figure 1:
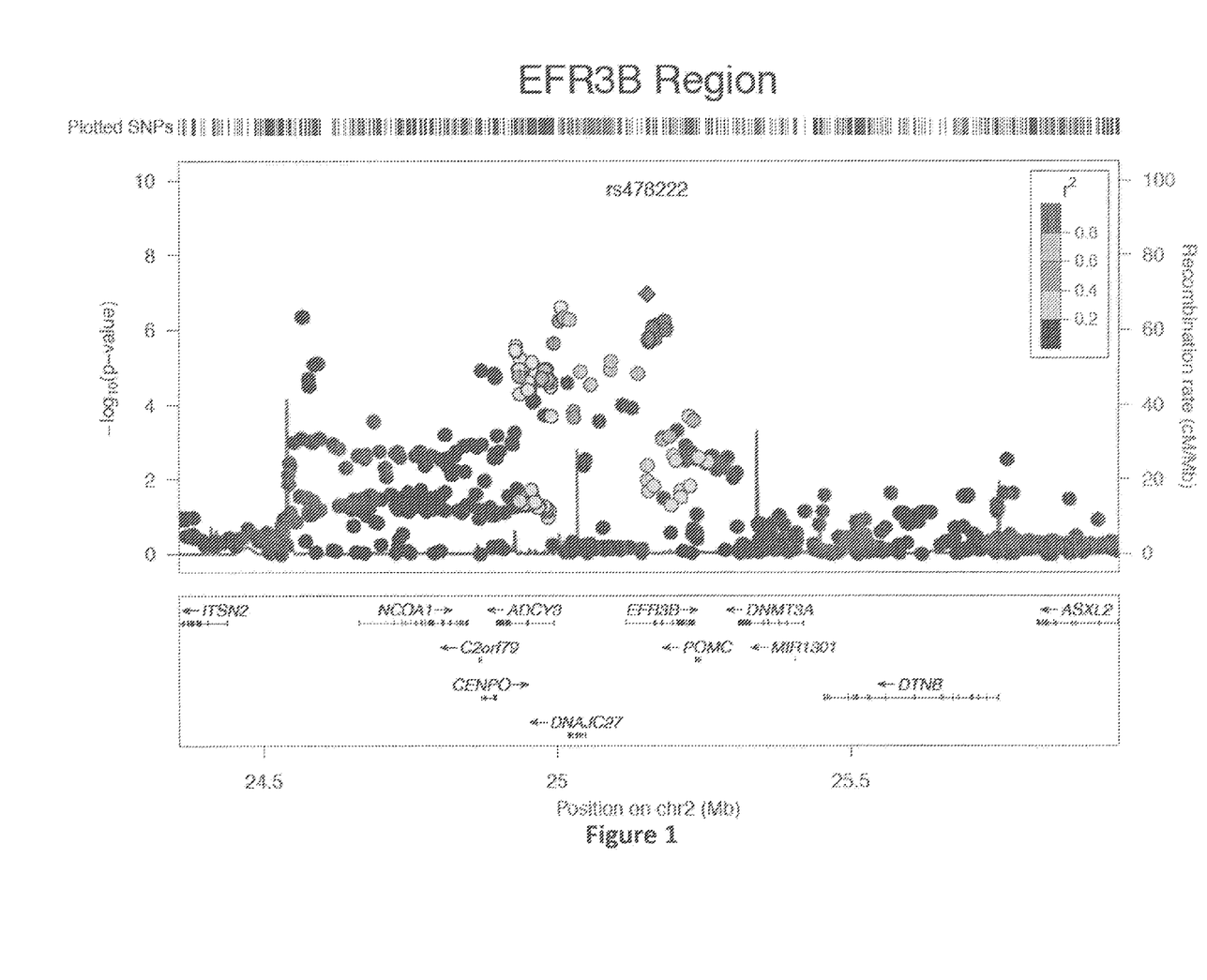
FIG. 1: Regional plot of the EFR3B associated region. −log 10 (P-values) for the discovery stage are shown for all SNPs in the region and color of circles indicates degree of LD with the most associated SNP in the region. Recombination rate is overlaid on the figure and the position with respect to genes is shown at the bottom.
Figure 2:
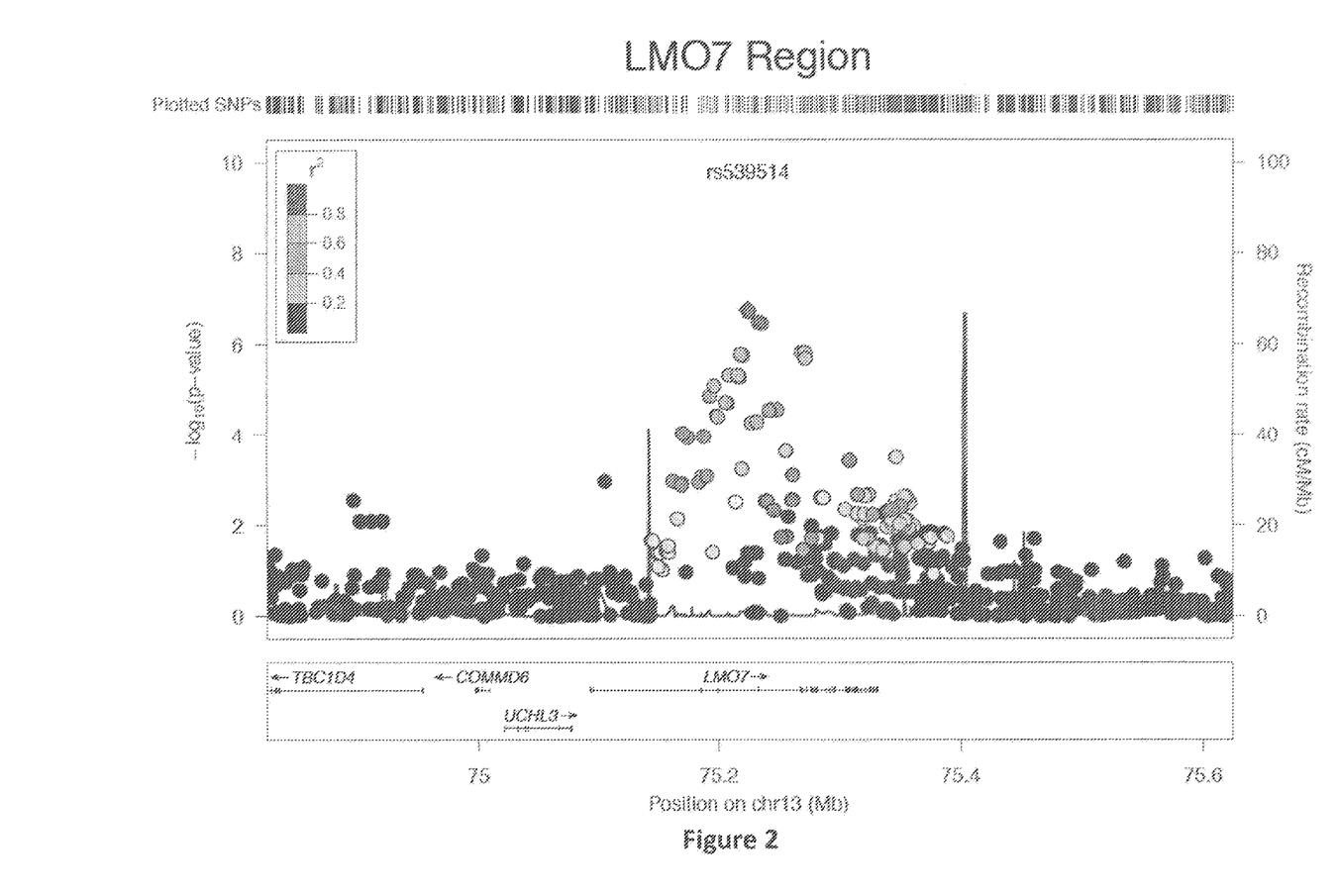
FIG. 2: Regional plot of the LMO7 associated region. −log 10 (P-values) for the discovery stage are shown for all SNPs in the region and color of circles indicates degree of LD with the most associated SNP in the region. Recombination rate is overlaid on the figure and the position with respect to genes is shown at the bottom.
Figure 3:
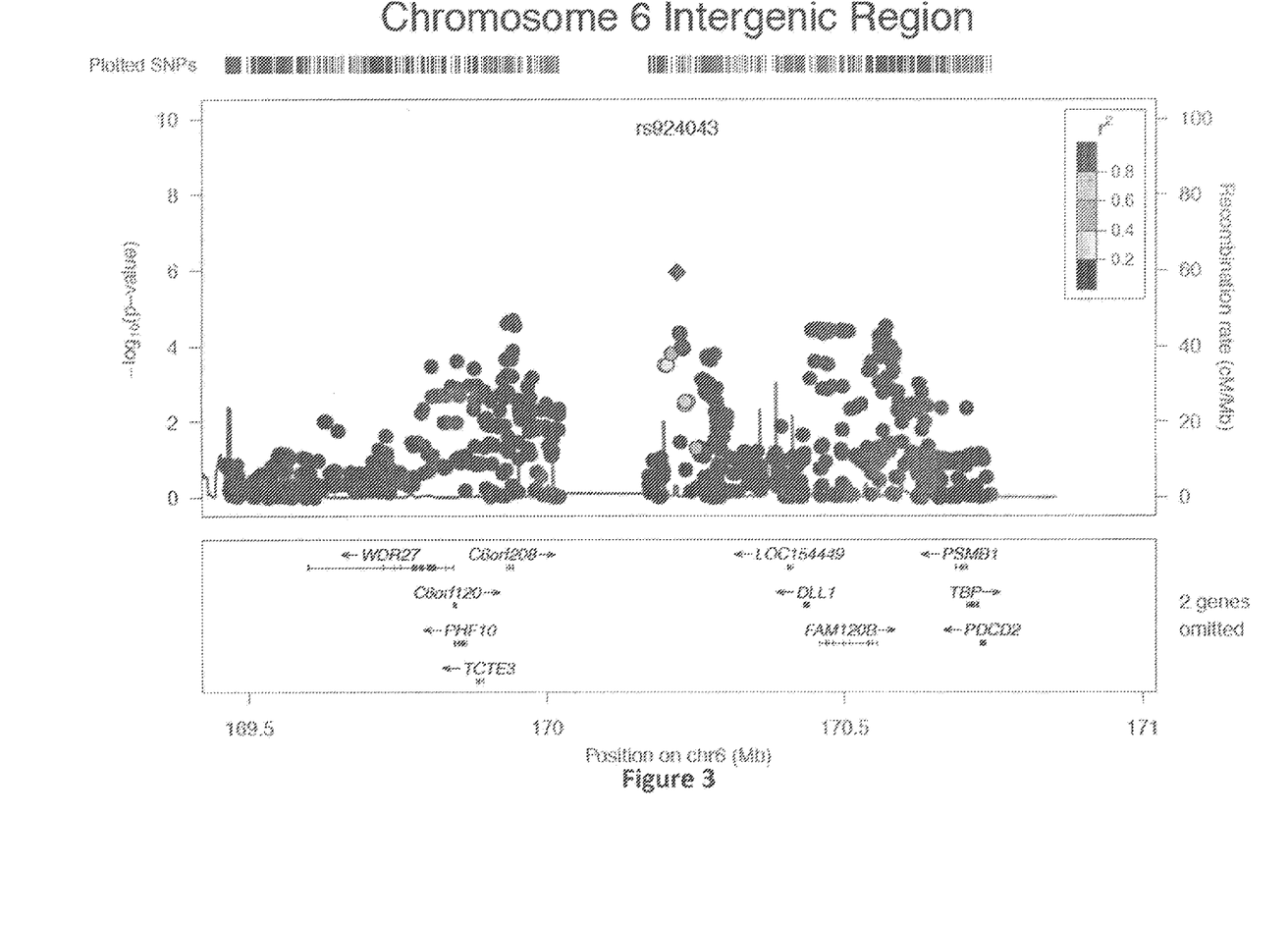
FIG. 3: Regional plot of the Chromosome 6 associated region. −log 10 (P-values) for the discovery stage are shown for all SNPs in the region and color of circles indicates degree of LD with the most associated SNP in the region. Recombination rate is overlaid on the figure and the position with respect to genes is shown at the bottom. Taken together, these results demonstrate that EFRB, LMO7 and the chromosome 6 locus associate with Type-1 diabetes (T1D) and these tagging SNPs will aid with determining T1D susceptibility in individuals at increased risk for the disease.

Three SNPs in previously unknown T1D loci replicated with a Fisher's combined $p<5.0\times10^{-08}$ and four SNPs in previously unknown loci showed suggestive replication in which the replication p-value was less than 0.05 but the combined p-value was more than the genome wide cut-off. One replicated SNP resides in region 13q22.2 in the gene LM07 and another in region 2p23.3 in the gene EFR3B. The last replicated SNP doesn't reside in a gene but is in region 6q27, which is also a linkage region known as IDDM8. See Table 1, and FIGS. 1, 2 and 3.

These results provide evidence for novel genetic factors that contribute to the pathogenesis of T1D, thus providing promising new T1D therapeutic and diagnostic targets.

TABLE 1

| SNP | Minor/Major Allele Replication | Transmitted Replication | Untransmitted Replication | OR Replication | CHISQ Replication | P Replication | Minor/Major Allele Meta-analysis | P Meta-analysis | OR Meta-analysis | P_COMBINED |
|---|---|---|---|---|---|---|---|---|---|---|
| rs539514 | T/A | 221 | 315 | 0.7016 | 16.49 | 4.90E−05 | T/A | 1.74E−07 | 0.8785 | 2.25E−10 |
| rs924043 | T/C | 224 | 294 | 0.7619 | 9.459 | 0.002101 | T/C | 1.12E−06 | 0.8353 | 4.93E−08 |
| rs478222 | T/A | 436 | 530 | 0.8226 | 9.147 | 0.002491 | T/A | 1.12E−07 | 0.8732 | 6.39E−09 |
| rs12679857 | G/A | 404 | 478 | 0.8452 | 6.209 | 0.01271 | G/A | 4.76E−06 | 0.8822 | 1.07E−06 |
| rs6547853 | A/G | 416 | 488 | 0.8525 | 5.735 | 0.01663 | A/G | 7.40E−06 | 0.8919 | 2.08E−06 |
| rs550448 | G/A | 203 | 248 | 0.8185 | 4.49 | 0.03409 | G/A | 7.70E−06 | 0.8468 | 4.24E−06 |
| rs235219 | A/G | 219 | 177 | 1.237 | 4.455 | 0.03481 | A/G | 3.92E−06 | 1.1895 | 2.29E−06 |

Example II

Standard convention for presenting the risk conferred by a given SNP is to describe the risk numerically for the less frequent allele in the population i.e. the minor allele. On occasions, the minor allele is less frequent in the cases than in the controls and therefore yields a risk of less than 1 (i.e. it is termed "protective"). In this event, it is the major, or more common, allele that confers risk. SNPs that show association are not necessarily causative themselves, rather they tag the mutation which must reside on a nearby region (i.e. within a few kilobases). The causative mutation itself may confer higher risk and be rarer. Thus, the SNP association essentially indicates that there is a causative mutation nearby and that this SNP-containing gene is involved in the pathogenesis of the disease and therefore can be utilized to detect susceptibility thereto.

Example III

The information herein above can be applied clinically to patients for diagnosing an increased susceptibility for developing T1D, and therapeutic intervention. A preferred embodiment of the invention comprises clinical application of the information described herein to a patient. Diagnostic compositions, including microarrays, and methods can be designed to identify the genetic alterations described herein in nucleic acids from a patient to assess susceptibility for developing T1D. This can occur after a patient arrives in the clinic; the patient has blood drawn, and using the diagnostic methods described herein, a clinician can detect a SNP in the LMO7 or EFR3B genes for example. The typical age range for a patient to be screened is between 9 and 12 years of age. The information obtained from the patient sample, which can optionally be amplified prior to assessment, will be used to diagnose a patient with an increased or decreased susceptibility for developing T1D. Kits for performing the diagnostic method of the invention are also provided herein. Such kits comprise a microarray comprising at least one of the SNPs provided herein in and the necessary reagents for assessing the patient samples as described above.

In another approach, the patient may have had previous genotyping performed and this genetic information is stored in a computer data file. Accordingly, the methods of the invention may be performed in silico wherein the SNP containing reference sequences are compared with patient sequences electronically stored to assess the same for the presence or absence of the SNPS disclosed herein thereby diagnosing an increased or decreased risk for developing T1D.

The identity of T1D-involved genes and the patient results will indicate which variants are present, and will identify those that possess an altered risk for developing T1D. The information provided herein allows for therapeutic intervention at earlier times in disease progression that previously possible. Also as described herein above, LMO7 and EFR3B provide novel targets for the development of new therapeutic agents efficacious for the treatment of T1D.

While certain of the preferred embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

What is claimed is:

1. A kit for use in a method for detecting genetic alterations in a target nucleic acid isolated from a patient for assessing susceptibility for developing type 1 diabetes (T1D), said kit comprising 1 diabetes (T1D), said kit comprising
   a solid support having a collection of SNP containing nucleic acids immobilized thereon, said SNP containing nucleic acids being associated with altered T1D risk, and functioning as primers or probes which are between 15-25 nucleotides in length, said collection having rs designations consisting of rs539514, rs924043, rs478222, rs12679857, rs6547853, rs550448 and rs235219.

2. The kit of claim 1, wherein said solid support is a microarray.

3. The kit of claim 1 further comprising reagents suitable for amplification of a nucleic acid obtained from a patient sample.

4. The kit of claim 1, wherein said solid support is a solid matrix selected from beads, microparticles, a microarray, the surface of a micro-titration well or test tube, a dipstick or a filter.

* * * * *